(12) United States Patent
Lussier

(10) Patent No.: US 8,249,308 B2
(45) Date of Patent: Aug. 21, 2012

(54) PORTABLE INTELLIGENT FLUORESCENCE AND TRANSMITTANCE IMAGING SPECTROSCOPY SYSTEM

(76) Inventor: Robert Lussier, Lexington, MA (US)

( * ) Notice: Subject to any disclaimer, the term of this patent is extended or adjusted under 35 U.S.C. 154(b) by 515 days.

(21) Appl. No.: 12/567,931

(22) Filed: Sep. 28, 2009

(65) Prior Publication Data

US 2010/0111369 A1 May 6, 2010

Related U.S. Application Data

(60) Provisional application No. 61/100,371, filed on Sep. 26, 2008.

(51) Int. Cl.
*G06K 9/00* (2006.01)
(52) U.S. Cl. ......................... 382/110; 356/300
(58) Field of Classification Search .................. 382/100, 382/110; 250/458.1, 459.1, 461.1, 461.2; 356/300, 317, 318, 417
See application file for complete search history.

(56) References Cited

U.S. PATENT DOCUMENTS

| | | | |
|---|---|---|---|
| 4,650,336 A * | 3/1987 | Moll | 356/417 |
| 6,121,053 A * | 9/2000 | Kolber et al. | 436/172 |
| 6,563,122 B1 * | 5/2003 | Ludeker et al. | 250/458.1 |
| 6,624,887 B1 * | 9/2003 | Kramer et al. | 356/326 |
| 6,813,024 B2 * | 11/2004 | Kramer et al. | 356/416 |
| 7,112,806 B2 * | 9/2006 | Lussier | 250/458.1 |
| 2001/0030742 A1 * | 10/2001 | Kramer et al. | 356/72 |
| 2009/0199470 A1 * | 8/2009 | Capen et al. | 47/58.1 LS |
| 2011/0018356 A1 * | 1/2011 | Chatterjee | 307/104 |

* cited by examiner

*Primary Examiner* — Anand Bhatnagar

(57) ABSTRACT

A portable fluorescence and transmittance imaging spectroscopy system for use in diagnosing plant health. The system has a primary LED light source array with spectral wavelengths in the 400-600 nm range, a focus cone that collects the LED light source output and focuses it, a controller that controls the primary LED array to turn it on and off, or certain of the spectral wavelengths on and off such that the primary LED array controllably emits light of a desired wavelength in the range, the light irradiating the plant through the focus cone, a digital imaging device that both spatially and temporally captures a fluorescence image comprising chlorophyll fluorescence emitted by the plant due to the emitted light from the LED array, a leaf holder located proximate to the output of the focus cone to maintain a consistent position and distance between the digital imaging device, the LED light source and the leaf and providing for fixed position and non-destructive leaf imaging and testing, a secondary light source for providing broad-band transmissive light through the leaf, a lens for focusing onto the imaging device the light emitted from the secondary light source, and one or more memory devices that store the fluorescence image and the transmitted light data received by the digital imaging device and store a library of plant fluorescence-intensity data indicative of both healthy plants and stressed or diseased plants, and plant light transmittance data indicative of certain plant conditions.

15 Claims, 2 Drawing Sheets

PORTABLE INTELLIGENT FLUORESCENCE AND TRANSMITTANCE IMAGING SPECTROSCOPY SYSTEM

CROSS-REFERENCE TO RELATED APPLICATION

This application claims priority to U.S. Provisional Patent Application Ser. No. 61/100,371, filed on Sep. 26, 2008, entitled "Intelligent Fluorescence Imaging Spectroscopy for Plant Disease and Stress." The contents of this priority application are expressly incorporated by reference herein.

FIELD OF THE INVENTION

This invention relates to a chlorophyll fluorescence imaging and computer processing system that measures, detects and quantifies plants under environmental and pathogenic stress and uses transmissive spectroscopy to obtain plant spectral signatures (data). Using expert computer software, the system compares the images and data to a plant disease library to diagnose the plant stress and disease instantly in the field.

BACKGROUND OF THE INVENTION

Chlorophyll Fluorescence Imaging Temporal (CFIT) described in U.S. Pat. No. 7,112,806 B2 (the '806 patent, incorporated herein by reference), images and quantifies chlorophyll fluorescence signal patterns, which measure and indicate whether the plant under test is healthy or diseased even though indications as to symptoms are not visible to the naked eye. CFIT images and measures the biology phenomenon of transient chlorophyll fluorescence with dark-adapted plants (Kautsky Effect). With a sensitive imager, active light and computer processing of the time-dependent chlorophyll fluorescence signatures, the resulting CFIT image-datacube spatially and temporally captures fluorescence-intensity-temporal (FIT) patterns that image and quantify plant stress as described in FIGS. 2, 3 and 4 of the '806 patent. The FIT patterns are real-time measures of electron transport and cellular pH that quantify the plant's photosynthetic response to plant stress. Eighteen different FIT patterns that relate to types and stages of plant health and pre-symptom plant stress have been identified in laboratory testing; such are disclosed in the '806 patent incorporated herein by reference. As the number of field crop applications and biotic and abiotic stressors increase, the number of foliar FIT patterns that are acquired and can be stored in an imaging system plant disease database will also increase, especially for biotic stress.

When conducting a CFIT testing (in the lab, greenhouse or field) many of the FIT patterns are general and not sufficient or specific to diagnose the cause or type of disease affecting the plant. Some are more specific and indicate an environmental stress such as a saturated herbicide pattern or another as a type of heat stress pattern. For other general FIT patterns additional secondary indicators are necessary to improve the diagnosis.

SUMMARY OF THE INVENTION

The invention comprises a portable CFIT instrument or system for imaging, processing and diagnosing FIT patterns, with additional secondary spectral indicators and expert (artificial intelligence) information software. The inventive system instantly diagnoses plant disease in the laboratory, greenhouse and the field, before disease symptoms are visible to the expert eye. Transmissive spectral signatures that are responsive to visible/near infrared (NIR) wavelength bands are used as a complement to the chlorophyll fluorescence emissions. When FIT signatures are combined with additional hyperspectral transmissive data, and compared to expert knowledge data, the result is a plant stress diagnostic that confirms a diagnosis of water stress, nutrient deficiency, toxic contaminants (e.g., arsenic and heavy metals), and pathogens, based on additional colors, lesions and/or spectral indicators detected by the FIT patterns and transmissive light data. The additional spectral information from fluorescence and transmissive spectroscopy with narrow-band wavelength signatures together with computer processing algorithms, enables this invention, a portable Intelligent Fluorescence Imaging Spectroscopy (IFIS) field system with hand-held imager and embedded computer, to image, quantify, and diagnose plant disease in the field, in real time.

This invention features a portable IFIS system with active light sources (light emitting diodes and other light sources), a sensitive imager such as an intensified CCD for imaging chlorophyll fluorescence signatures and multi-spectral wavelength information from interference filters carried by a filter wheel, and devices to interface the video data stream to a hard-wired, digital/video capture board (or wireless controller that transmits the data to a remote computer) to an embedded or portable computer. The inventive system images the plant-under-test while the plant (or its portions being imaged) is shielded from ambient light or under a temporary shroud. The system acquires the dark-adapted, time-dependent fluorescence measurements and transmissive spectral data as a combined plant stress diagnostic and stores the data in the system's buildable database. The diagnostic information is then matched against a disease library in the system database to diagnose plant disease before the disease symptoms are visible to the expert eye.

The inventive IFIS detects and diagnoses plant stress in part using visible light in the 400-600 nm range. This light induces 690 nm red fluorescence from the plant. The system detects this fluorescence, as an image that can be indicative of plant stress as disclosed in the '806 patent incorporated herein by reference. The imaging permits the location and interactive selection of the maximum stress intensity on the leaf. This effectively calibrates the FIT stress signatures and diagnostics as maximal signals for comparison to like signals stored in the disease database. Prior art systems/technologies that are non-imaging must take single-point data selection across the leaf. If the analysis is restricted to photosynthetic activity this may be satisfactory. If the analysis is for stress, single-point data selection is inadequate, because chlorophyll is not uniform across the leaf and the measure can miss the pre-symptom stress, which usually occurs near the outer rim of the leaf. As such, a stress measurement with single-point data selection can be completely erroneous.

An embodiment of the inventive IFIS system is a hand-held, active light multi-spectral, sensitive CCD imager with embedded computer. The system uses a primary visible light source, preferably of a light-emitting-diode array that provides spectral light at 400, 420, 470, 530, 600 nm or B-G-Y light from 400 nm to 600 nm. The spectra are the same as the mercury halide lamp used for CFIT testing in the referenced '806 patent. A LED controller can turn the LED array on-off, or individual LED spectra on-off. The system uses a two-dimensional CCD imaging device to acquire chlorophyll fluorescence emissions as a CFIT video-data stream at 690 nm (PSII) and 740 nm (PSI) via the use of narrow-band (10 nm) filters, as in the referenced '806 patent. CFIT digital processing converts the video-data stream to a fluorescence x, y, t image-datacube with stacked video frames digitized in false colors that depict the leaf plant stress pattern and intensity with five colors (black-ref., blue-low, white-moderate, red-high, and green-highest/saturation). The system can interrogate this data cube to measure at any image pixel, the changes over time of the test plant's transient chlorophyll fluorescence emissions. The CFIT test graphically measures plant stress and the deterioration of photosynthetic efficiency with FIT. The 690 nm red fluorescence band (PSII) is the principal CFIT stress measurement and images and quantifies the test plant's stress condition as either biotic or abiotic stress conditions. The stress condition diagnosis can be based on the initial rise-time to fluorescence peak, Fp, (electron transport response) and quenching or decay-time from fluorescence peak, Fp, to steady-state, Fs (cellular pH response). Electron transport response assists to identify plant damage. A slow decay time assists to identify pathogen stress. These measures are disclosed in the '806 patent incorporated herein by reference. CFIT also images and visualizes unseen lesions (virtual lesions) and leaf physiological responses (e.g., color, bleaching, curl, wilt) as with pathogen stresses, allowing the diagnosis as pre-symptom, advanced and visible/lethal plant stress.

This invention uses additional computer algorithms and multi-spectral data to diagnose a CFIT plant stress condition and so determine the type and cause of the plant disease. The inventive IFIS system also acquires transmissive spectroscopy signatures that are compatible to a sensitive, intensified CCD image detector. A secondary broad-band light source, such as a tungsten halogen lamp, is used to provide the source for the transmissive spectroscopy. The light, which may be delivered via fiber optics or other means, is directed through the leaf to return transmissive spectral light that is transmitted through the leaf toward the imager-detector. A variable light intensity due to cellular stress or disease stimuli is obtained in the wavelength bands in the spectral regions of interest. Multiple spectral bands may be tested by using a filter-wheel with a plurality of narrow band interference filters, or with a spectral grating spectrometer or a photo-diode array-based detector.

The visible/near infrared (NIR) transmissive spectral band(s) selected for diagnosis via narrow band filters are captured by detector and memory. The results are used to determine and measure the plant's real-time physiological response, and enable the acquisition of additional spectral data to diagnose the plant stress condition. The wavelength bands selected in the preferred embodiment are from 400 nm to 1000 nm (for silicon-based detector). These wavelengths are effective to measure leaf water moisture, chlorophyll yield, and nutrient deficiency of potassium, phosphorous, iron, zinc, and magnesium, as examples. NIR spectral bands from 900 nm to 2500 nm are effective to measure additional photosynthetic pathways for carbohydrate, glucose, sucrose, protein, and starch, to provide additional NIR plant-disease and quality yield information. The absorption of water is also strong at 1400 nm and 2100 nm in this spectral range. The 900-2500 spectral bands are best detected with a spectral grating spectrometer or a photodiode array (InGaAs; PbS).

The FIT and transmissive spectral data are then characterized using an expert computer algorithm (e.g., a hybrid-artificial intelligence software) that summarily weighs the total information of plant species, fluorescence stress data, photosynthetic spectral wavelength signatures, leaf physiology, environmental information, and together with FIT image-data of virtual and actual plant lesions, diagnoses the cause of a plant disease, pre-symptom. The system can accept this additional data from the user, or from other sources such as a remote or local networked computer. The system either automatically or with user guidance performs the diagnosis.

The embedded or portable computer stores and then compares the spectral band signatures and expert diagnostic information to a buildable plant disease library that is maintained and supported by other computers via Internet connectivity, and/or the local computer, to diagnose the disease type. With a buildable plant disease library, an IFIS system has application for instantly diagnosing all types of plant disease in the field. With computer speed, access and data storage, the IFIS expert algorithm enables a real-time, in situ diagnosis of pre-symptom plant disease.

This invention features a portable fluorescence and transmittance imaging spectroscopy system for use in diagnosing plant health that is used along with an enclosure or shroud for placement around all or a portion of one or more plants or leaves to shield them from ambient light during the daytime and allow the plants or leaves to be imaged in situ, comprising a primary LED light source array with spectral wavelengths in the 400-600 nm range, a focus cone that collects the LED light source output and focuses it, to create a relatively balanced LED light intensity at its output, a controller that controls the primary LED array to turn it on and off, or certain of the spectral wavelengths on and off such that the primary LED array controllably emits light of a desired wavelength in the range, the light irradiating the plant through the focus cone, a digital imaging device that both spatially and temporally captures a fluorescence image comprising chlorophyll fluorescence emitted by the plant due to the emitted light from the LED array, a leaf holder located proximate to the output of the focus cone and constructed and arranged such that it can be temporarily coupled to a leaf, for maintaining a consistent position and distance between the digital imaging device, the LED light source and the leaf and providing for fixed position and non-destructive leaf imaging and testing, a secondary light source for providing broad-band transmissive light through the leaf, a lens for focusing onto the imaging device the light emitted from the secondary light source of a particular wavelength range that is transmitted through the leaf, and one or more memory devices that store the fluorescence image and the transmitted light data received by the digital imaging device, and store a library of plant fluorescence-intensity data indicative of both healthy plants and stressed or diseased plants, and plant light transmittance data indicative of certain plant conditions.

The system may further comprise a processor that in conjunction with a database accomplishes the comparison of the stored fluorescence image and the stored transmittance data to the library data, and diagnoses the plant's health and condition based on the matching, near-matching or non-matching of the stored fluorescence image and the stored transmittance data to the library data. The system may further comprise a filter wheel carrying a plurality of narrow band filters located in the path between the secondary light source and the digital imaging device, for use in selecting one or more transmitted wavelength bands to be captured by the imaging device.

The library may comprise a plant stress database comprising fluorescence-intensity-time (FIT) images and information regarding the plant stresses that result in such images. The library may further comprise a plant disease database comprising transmissive spectral data and information regarding plant diseases that result in such data. The library may further comprise additional data relating to one or more of plant photosynthetic spectral wavelength signatures, leaf physiology, environmental information and visual plant image data. The comparison accomplished by the processor may include comparison of collected data to the additional data in the library.

The output of the secondary light source may be carried by the leaf holder. The leaf holder may be pivotally or magnetically coupled to the focus cone. The LED array may be located in a ring surrounding the lens.

BRIEF DESCRIPTION OF THE DRAWINGS

The foregoing and other objects, features and advantages of the invention will be apparent from the following more particular description of preferred embodiments of the invention, as illustrated in the accompanying drawings, in which:

FIGS. 2-5 are FIT images illustrating the results of stress and disease, in which FIG. 2 shows an early lesion from Phytophthora pathogen, with FIG. 2A showing stress on the leaf and FIG. 2B showing an unseen lesion FIG. 3 also shows an early lesion from Phytophthora pathogen when the lesion is first visible with necrosis, FIG. 4 shows nitrogen deficiency on corn, and FIG. 5 shows nitrogen deficiency on bean.

DESCRIPTION OF THE PREFERRED EMBODIMENTS OF THE INVENTION

Figure 1:
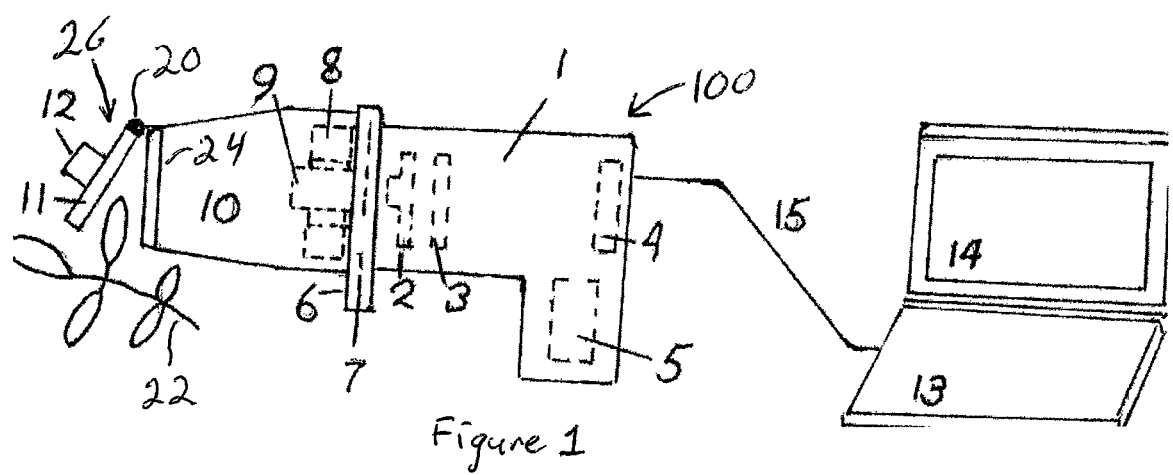
FIG. 1 is a schematic diagram of the preferred embodiment of the inventive system.

As shown in FIG. 1, the inventive portable IFIS system 100 comprises a hand-held enclosure 1, sensitive multi-pixel, two-dimensional CCD imager 2, a hard-wired interface 4 or wireless communications link 15, and a portable computer 13 with solar display 14 that may be used in bright sunlight, carried and positioned near the plants to be tested, or worn by the operator. Alternatively, the system can be fully self-contained in terms of memory and computing power, i.e., the necessary functionality from computer 13 can be built into or built as a unit along with enclosure 1.

The hand-held enclosure carries light focusing lens 9, one or more narrow-band Fabry-Perot interference filters 7 carried by a manual or motorized filter-wheel 6 that holds "n" interference filters, and a digital imaging, controller and memory board 3 that controls operation of the system and stores the data, as necessary in conjunction with computer 13; this board can alternatively carry sufficient memory and computing devices to augment or replace the functionality of computer 13. A light focus cone 10 carries within it an LED array or ring light 8. The combination of these two provides balanced light in one or more spectra in the 400 to 600 nm range to the leaf. The focus cone provides even balanced light at the optimal distance from lens to the leaf and assures that all plant images are uniform for capture and recording to the database.

Leaf unit 26 is an extension of the hand-held unit 1 (and can be attached to it at pivot 20) and includes an annular soft-faced (so as not to damage the plant) leaf-holder 11 that holds one or more leaves or other portions of plant 22 against the rim 24 at the open circular narrow end of cone 10. Leaf holder 11 can additionally (or alternatively) be selectively coupled to rim 24 using magnets, as in a refrigerator seal. Leaf unit 26 also comprises a broad-band transmissive light source 12 that can be supplied with light via fiber optic or other means. A power module 5 provides battery power to the hand-held imager and the light sources.

Operation

This invention results from the realization that a portable IFIS field system can provide the commercial grower or other end-user (researcher, ecologist/biologist) with a real-time, non-destructive image capture and test and analysis of plant health in the field using the CFIT testing means and FIT patterns together with hyperspectral leaf transmissive signatures. The testing can be of whole plants, or one or more leaves. The IFIS processing quantifies and compares the digitized image-data signatures using expert software and a computer database (carried by board 3 and/or computer 13), enabling the user to diagnose plant health and pre-symptom plant disease for new field management with curative controls to avoid disease loss and increase crop yield. A temporary shroud (not shown) is used to cover one or more field plants or leaves to be tested. After the dark-adapt-time of 3 minutes or more depending on the plant species a portion of plant 22 is placed in clamping leaf holder 11. Leaf holder 11 assures that the leaf orientation is correct, that the leaf is not physically damaged, and that the leaf remains dark adapted. Hand-held imager 1, (which as necessary can be held and stabilized by a pole extender under the shroud) is then used to test the leaf. The computer (either computer 13 or an on-board captive computer) controls the system to image, quantify and record the plant stress image in false color. The image is displayed to the user on the computer display.

The first indication of a plant stress is a CFIT, false color image of an unseen or pre-symptom leaf stress pattern that is highlighted by the computer in green/red/white/blue color. In certain instances a virtual lesion may be evident, which provides an immediate diagnosis of a pathogen stress. The lesion image pattern can be compared to a pathogen database for a disease match.

Figure 2A:
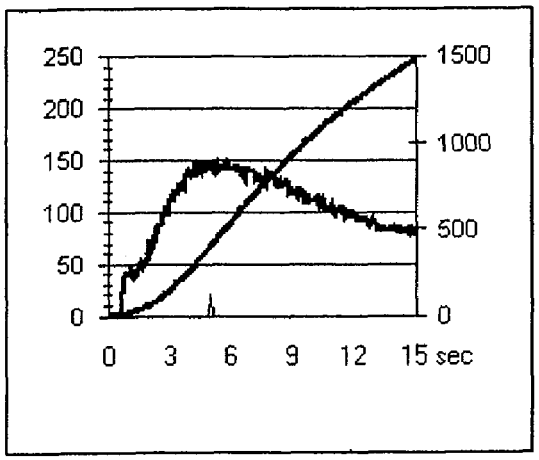
Figure 2B:
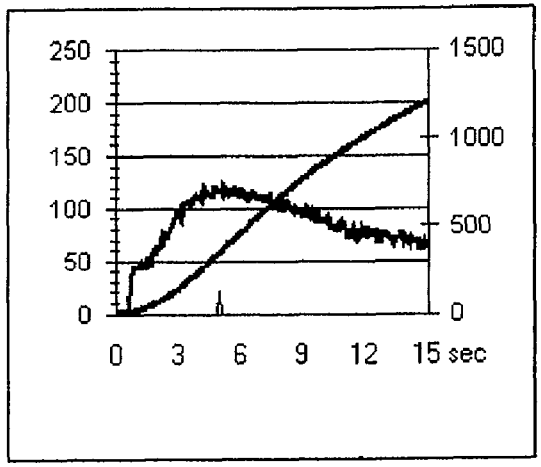
Figure 3:
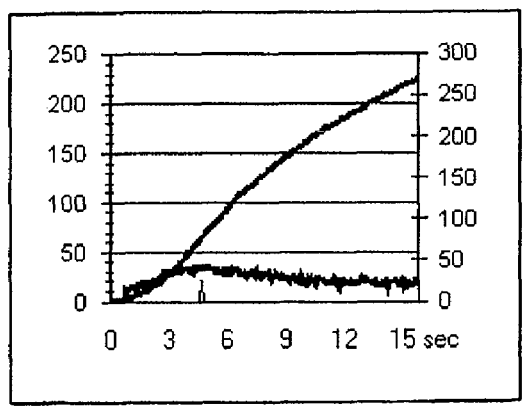

A virtual lesion is an early forming lesion, which CFIT can visually detect. An x-y pixel selection will call a FIT measure of the lesion and confirm its status as early, advanced or critical. The continuing diagnosis will then concentrate on the type of pathogen. The knowledge data file will provide information on the known plant species and the affecting pathogens that have lesions. The software algorithm will suggest additional tests with comparison data (size, pattern, color) to finally diagnose the disease. FIG. 2 is an example of a CFIT image of a virtual lesion with FIT graphics. FIG. 2B shows a FIT measure of the virtual lesion. FIG. 3 shows a FIT measure when the lesion is first visible and necrotic. Note that the images in FIGS. 2-5 are of the same type and display the same types of data as in the referenced '806 patent (fluorescence image magnitude over time and first integral over time at one selected pixel (x-y position) of the two-dimensional CCD imager.

Figure 4:
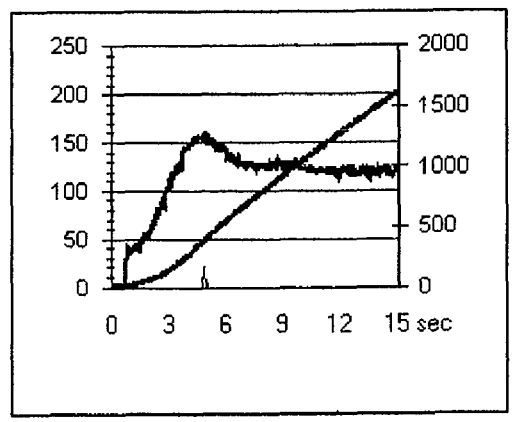

If the CFIT plant stress image does not contain a virtual lesion, the detected stress may be any pre-symptom disease. The preferred embodiment of the diagnosis of the stress image is as follows. Where the false color image indicates a high stress intensity (e.g., red at one or more pixels), the user selects the pixel at the maximum stress and the calibrated FIT pattern is displayed, as in FIGS. 2-5. The FIT pattern is then compared to the plant stress database. An exact FIT match will diagnose the disease or a near-match or a no-match will indicate the need for further testing. FIGS. 3b, 3c, of the referenced '806 patent are examples of general FIT patterns for environmental stress. FIGS. 3d, 3e are general FIT patterns of water stress or pathogen stress. FIGS. 4B, 4C, and 4D of the referenced '806 patent illustrate this further as general FIT patterns for bean drought stress.

Fiber-optic supplied or direct light source 12 provides transmissive light through the under-part of the leaf held in the leaf holder, through lens 9, filter wheel 6 and into CCD 2. The system records the transmissive spectral leaf data, which can be in one or more desired narrow bands (accomplished with one or more of filters 7). The expert software interactively guides the operator through several spectral data selections, or accomplishes this automatically, and then compares the image-data (FIT plus transmissive, plus knowledge data) to the stored plant disease standards in the library, which contains leaf transmissive data from plants with known diseases, to diagnose the plant disease. The plant disease library is a buildable disease library and can be supported and maintained in the field or via the Internet.

In the case of bean drought stress illustrated in the referenced '806 patent, a transmissive test of 970 nm detected in the plant will immediately determine low-water moisture and confirm the test as bean drought stress. A bean FIT pattern that matches FIG. 4E of the referenced '806 patent is a healthy bean plant.

Figure 5:
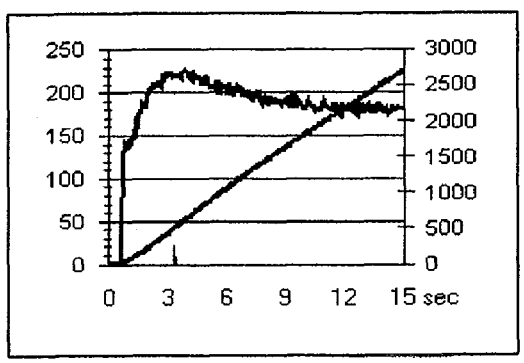

FIG. 4 herein is a CFIT datacube image and FIT measure of nitrogen deficiency in corn. FIG. 5 is a CFIT datacube image and FIT measure of nitrogen deficiency in bean. In both cases, a secondary transmissive test at 530 nm will confirm the nitrogen deficiency from chlorophyll yield.

In all cases the FIT patterns can be characterized by intensity-time measurements of the fluorescence signal's rise-time from Fo (first energy step) to Fp (peak), and which describes the electron transport response to stress in PSII. The fluorescence signal's decay or quenching time from Fp to Fs (steady state) provides information on how the stress response affects the plant's thylakoid cells. A continuing stress also impacts the fate of chlorophyll yield, killing off pigments so that the fluorescence emission is reduced. This is especially true in a pathogen response. FIT truncates the test at 15 seconds as the stress information, electron transport and quenching, is completed. User selection can extend or shorten the test duration.

The embodiment of the inventive test system will test dark-adapted plants with CFIT techniques, and compare the FIT patterns to the plant stress database. If the secondary testing is indicated (no FIT match), the system acquires the additional transmissive signatures using the secondary broad-band light source. Interference filters in the filter wheel can be used to narrow-band select different desired spectral bands of transmissive light, such as 970 nm for water leaf moisture, and 530 nm for chlorophyll yield. The CCD detector (silicon) with correct spectral sensitivity is useful to detect both water leaf moisture (indicative of water stress) and nutrient deficiency including nitrogen (from chlorophyll yield algorithm) and the nutrients phosphorus, potassium, iron and zinc. The CCD detector is also used to measure other leaf disease colors or spectral data and calibrate the intensity of the transmitted light. Other spectral transmissive bands useful to diagnose a specific crop disease may be enabled, for example, 900 nm to 1700 nm (using In—Ga—As detector). The spectral range will enable other NIR bands to confirm a FIT pattern.

The expert computer algorithm (a hybrid knowledge-based or artificial intelligence software) will characterize the fluorescence measurement, the additional transmissive signatures, the known plant species, environmental and specific site information (e.g., rain fall, fertilization, temperature) as input by the user or automatically via sensors or connections to remote data sources, and image-data of "virtual" and/or visible data of plant disease lesions that are stored in memory. The software compiles this data into a search disease diagnostic. The system then tests the database for a match in order to determine the cause of the disease.

The computer will compare the search disease diagnostic to a buildable plant disease library that comprises "standard disease diagnostics" and is maintained and supported in the field to diagnose disease. The system then compares the match of the test search diagnostic to the "standard disease" in the library. An exact match will determine the disease cause. Statistical prediction (regression analysis) may be used for near-matches.

The expert computer diagnostic algorithm will diagnose plant disease in a subtractive test. The FIT pattern will first be characterized from rise-time and fall-time measures and then tested and compared to the FIT database for exact or near-matches. Success will diagnose the disease with an exact match or determine near-matches or no-match. The testing will then continue with transmissive testing.

The first transmissive test will test for leaf water moisture, 970 nm. If the result is a low moisture, the FIT pattern will be compared to the water stress category in the plant species database. An exact match will indicate the stress is water stress and the search will stop. A non-match can mean there is a root pathogen stress. The expert diagnostic would then test root pathogens in the species database. If this also failed (no match), the expert diagnostic would then test pathogens in the database. If there were no match again, the system could then add the FIT pattern as a new disease in the category of the nearest match.

The next transmissive test is for nutrient deficiency, 530 nm, which relates strongly to nitrogen deficiency. An exact match would diagnose the stress and stop the search. If there was no match, the FIT pattern could be tested across the entire database, insects and environmental contaminants. A continued no-match, could then cause the system to conduct a full hyperspectral range test from 900 nm to 1700 nm and if necessary 900 nm to 2500 nm. The hyperspectral values can be used to diagnose any disease dependent on the additional detail involved.

The particular construction, materials and dimensions described herein are not limitations of the invention, as other constructions can accomplish the invention described herein.

Although specific features of the invention are shown in some figures and not others, this is for convenience only, as some features may be combined with any or all of the other features in accordance with the invention.

Recitation ranges of values herein are merely intended to serve as a shorthand method of referring individually to each separate value falling within the range, unless otherwise indicated herein, and each separate value is incorporated into the specification as if it were individually recited herein.

The use of any and all examples, or exemplary language (e.g., "such as") provided herein, is intended merely to better illustrate the invention and does not pose a limitation on the scope of the invention.

A variety of modifications to the embodiments described herein will be apparent to those skilled in the art from the disclosure provided herein. Thus, the invention may be embodied in other specific forms without departing from the spirit or essential attributes thereof.

What is claimed is:

1. A portable fluorescence and transmittance imaging spectroscopy system for use in diagnosing plant health that is used along with an enclosure or shroud for placement around all or a portion of one or more plants or leaves to shield them from ambient light during the daytime and allow the plants or leaves to be imaged in situ, comprising:
    a) a primary LED light source array with spectral wavelengths in the 400-600 nm range;
    b) a focus cone that collects the LED light source output and focuses it, to create a relatively balanced LED light intensity at its output;
    c) a controller that controls the primary LED array to turn it on and off, or certain of the spectral wavelengths on and off such that the primary LED array controllably emits light of a desired wavelength in the range, the light irradiating the plant through the focus cone;

d) an imaging device that both spatially and temporally captures a fluorescence image comprising chlorophyll fluorescence emitted by the plant due to the emitted light from the LED array;

e) a leaf holder located proximate to the output of the focus cone and constructed and arranged such that it can be temporarily coupled to a leaf, for maintaining a consistent position and distance between the digital imaging device, the LED light source and the leaf and providing for fixed position and non-destructive leaf imaging and testing;

f) a secondary light source for providing broad-band transmissive light through the leaf;

g) a lens for focusing onto the imaging device both the fluorescence emitted by the plant due to the emitted light from the LED array and the light emitted from the secondary light source of a particular wavelength range that is transmitted through the leaf; and h) one or more memory devices that store the fluorescence image and the transmitted light data received by the imaging device, and store a library of plant fluorescence-intensity data indicative of both healthy plants and stressed or diseased plants, and plant light transmittance data indicative of certain plant conditions.

2. The system of claim 1 further comprising a processor that in conjunction with a database accomplishes the comparison of the stored fluorescence image and the stored transmittance data to the library data, and diagnoses the plant's health and condition based on the matching, near-matching or non-matching of the stored fluorescence image and the stored transmittance data to the library data.

3. The system of claim 2 further comprising a filter wheel carrying a plurality of narrow band filters located in the path between the secondary light source and the imaging device, for use in selecting one or more transmitted wavelength bands to be captured by the imaging device.

4. The system of claim 2 in which the library comprises a plant stress database comprising fluorescence-intensity-time (FIT) images and information regarding the plant stresses that result in such images.

5. The system of claim 4 in which the library further comprises a plant disease database comprising transmissive spectral data and information regarding plant diseases that result in such data.

6. The system of claim 5 in which the library further comprises additional data relating to one or more of plant photosynthetic spectral wavelength signatures, leaf physiology, environmental information and visual plant image data.

7. The system of claim 6 in which the comparison accomplished by the processor includes comparison of collected data to the additional data in the library.

8. The system of claim 1 in which the output of the secondary light source is carried by the leaf holder.

9. The system of claim 8 in which the leaf holder is pivotally or magnetically coupled to the focus cone.

10. The system of claim 1 in which the LED array is located in a ring surrounding the lens.

11. The system of claim 1 in which the imaging device is a digital imaging device.

12. The system of claim 11 in which the digital imaging device is a CCD.

13. A portable fluorescence and transmittance imaging spectroscopy system for use in diagnosing plant health that is used along with an enclosure or shroud for placement around all or a portion of one or more plants or leaves to shield them from ambient light during the daytime and allow the plants or leaves to be imaged in situ, comprising:

a) a primary LED light source array with spectral wavelengths in the 400-600 nm range;

b) a focus cone that collects the LED light source output and focuses it, to create a relatively balanced LED light intensity at its output;

c) a controller that controls the primary LED array to turn it on and off, or certain of the spectral wavelengths on and off such that the primary LED array controllably emits light of a desired wavelength in the range, the light irradiating the plant through the focus cone;

d) a digital imaging device that both spatially and temporally captures a fluorescence image comprising chlorophyll fluorescence emitted by the plant due to the emitted light from the LED array;

e) a leaf holder located proximate to the output of the focus cone and selectively coupled to the focus cone and constructed and arranged such that it can be temporarily coupled to a leaf, for maintaining a consistent position and distance between the digital imaging device, the LED light source and the leaf and providing for fixed position and non-destructive leaf imaging and testing;

f) a secondary light source for providing broad-band transmissive light through the leaf, in which the output of the secondary light source is carried by the leaf holder;

g) a lens for focusing onto the imaging device at least the fluorescence emitted by the plant due to the emitted light from the LED array, in which the LED array is located in a ring surrounding the lens;

h) a filter wheel carrying a plurality of narrow band filters located in the path between the secondary light source and the digital imaging device, for use in selecting one or more transmitted wavelength bands to be captured by the imaging device;

i) one or more memory devices that store the fluorescence image and the transmitted light data, and store a library of plant fluorescence-intensity data indicative of both healthy plants and stressed or diseased plants, and plant light transmittance data indicative of certain plant conditions, in which the library comprises a plant stress database comprising fluorescence-intensity-time (FIT) images and information regarding the plant stresses that result in such images and a plant disease database comprising transmissive spectral data and information regarding plant diseases that result in such data; and j) a processor that in conjunction with the database accomplishes the comparison of the stored fluorescence image and the stored transmittance data to the library data, and diagnoses the plant's health and condition based on the matching, near-matching or non-matching of the stored fluorescence image and the stored transmittance data to the library data, in which the comparison accomplished by the processor includes comparison of collected data to the additional data in the library.

14. The system of claim 13 in which the secondary light source emits light in the range of 400 nm to 1000 nm, and the digital imaging device receives both the fluorescence emitted by the plant due to the emitted light from the LED array, and the transmitted light passed through the leaf.

15. The system of claim 13 in which the secondary light source emits light in the range of 900 nm to 2500 nm, the digital imaging device receives the fluorescence emitted by the plant due to the emitted light from the LED array, and the system further comprises a separate detector for detecting the transmitted light passed through the leaf.

* * * * *